(12) United States Patent
Friedman et al.

(10) Patent No.: US 11,697,024 B2
(45) Date of Patent: Jul. 11, 2023

(54) DEVICES AND METHODS FOR CARDIAC PACING AND RESYNCHRONIZATION

(71) Applicant: Mayo Foundation for Medical Education and Research, Rochester, MN (US)

(72) Inventors: Paul A. Friedman, Rochester, MN (US); Charles J. Bruce, Ponte Verda, FL (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 365 days.

(21) Appl. No.: 16/998,140

(22) Filed: Aug. 20, 2020

(65) Prior Publication Data

US 2020/0376274 A1    Dec. 3, 2020

Related U.S. Application Data

(62) Division of application No. 15/497,432, filed on Apr. 26, 2017, now Pat. No. 10,780,280.

(60) Provisional application No. 62/327,862, filed on Apr. 26, 2016.

(51) Int. Cl.
| | |
|---|---|
| *A61N 1/368* | (2006.01) |
| *A61N 1/375* | (2006.01) |
| *A61N 1/372* | (2006.01) |
| *A61N 1/05* | (2006.01) |
| *A61N 1/365* | (2006.01) |

(52) U.S. Cl.
CPC ........... *A61N 1/3684* (2013.01); *A61N 1/057* (2013.01); *A61N 1/36564* (2013.01); *A61N 1/3756* (2013.01); *A61N 1/37217* (2013.01)

(58) Field of Classification Search
CPC .. A61N 1/3684; A61N 1/057; A61N 1/36564; A61N 1/37217; A61N 1/3756; A61N 1/37518
See application file for complete search history.

(56) References Cited

U.S. PATENT DOCUMENTS

| | | | |
|---|---|---|---|
| 4,971,070 | A | 11/1990 | Holleman et al. |
| 5,683,429 | A | 11/1997 | Mehra |
| 7,389,134 | B1 | 6/2008 | Karicherla et al. |
| 7,532,933 | B2 | 5/2009 | Hastings et al. |
| 7,634,319 | B2 | 12/2009 | Schneider et al. |
| 8,014,865 | B2 | 9/2011 | Najafi et al. |
| 8,021,359 | B2 | 9/2011 | Auth et al. |
| 8,204,605 | B2 | 6/2012 | Hastings et al. |
| 8,303,511 | B2 | 11/2012 | Eigler et al. |
| 10,118,026 | B2 | 11/2018 | Grubac et al. |
| 2003/0078465 | A1 | 4/2003 | Pai et al. |

(Continued)

*Primary Examiner* — Mark W. Bockelman
(74) *Attorney, Agent, or Firm* — Fish & Richardson P.C.

(57) ABSTRACT

Devices and methods can be used for artificial cardiac pacing and/or resynchronization. For example, this document provides improved electrodes for stimulating and sensing electrical activity of the heart, and provides pacing and resynchronization systems incorporating such electrodes. While the devices and methods provided herein are described primarily in the context of pacing, it should be understood that resynchronization can additionally or alternatively be performed in an analogous manner, and that the scope of this disclosure includes such subject matter.

18 Claims, 4 Drawing Sheets

(56) References Cited

U.S. PATENT DOCUMENTS

| | | |
|---|---|---|
| 2004/0147973 A1 | 7/2004 | Hauser |
| 2005/0136385 A1* | 6/2005 | Mann ..................... A61N 1/025 434/320 |
| 2007/0150009 A1 | 6/2007 | Kveen et al. |
| 2008/0119911 A1 | 5/2008 | Rosero |
| 2009/0143835 A1 | 6/2009 | Pastore et al. |
| 2009/0171408 A1 | 7/2009 | Solem |
| 2010/0069983 A1 | 3/2010 | Peacock et al. |
| 2010/0094367 A1 | 4/2010 | Sen |
| 2010/0286744 A1 | 11/2010 | Echt et al. |
| 2011/0245842 A1 | 2/2011 | Liang |
| 2012/0265296 A1 | 10/2012 | McNamara et al. |
| 2012/0283585 A1 | 11/2012 | Werneth et al. |
| 2013/0066399 A1 | 3/2013 | Min |
| 2013/0338706 A1 | 12/2013 | Jimenez et al. |
| 2017/0304624 A1 | 10/2017 | Friedman et al. |

\* cited by examiner

DEVICES AND METHODS FOR CARDIAC PACING AND RESYNCHRONIZATION

CROSS REFERENCE TO RELATED APPLICATIONS

This application is a divisional of U.S. application Ser. No. 15/497,432 filed on Apr. 26, 2017, which claims the benefit of U.S. Provisional Application No. 62/327,862 filed Apr. 26, 2016. The disclosure of the prior applications are considered part of and are incorporated by reference in the disclosure of this application.

BACKGROUND

1. Technical Field

This document relates to devices and methods for artificial cardiac pacing and/or resynchronization. For example, this document relates to improved electrodes for stimulating and sensing electrical activity of the heart, and to pacing and resynchronization systems incorporating such electrodes.

2. Background Information

A pacemaker system is a small, battery-operated device that senses when a heart is beating irregularly or too slowly. The pacemaker system can also generate and deliver pulse signals to the heart to induce the heart to beat at the correct pace.

The primary purpose of a pacemaker is to maintain an adequate heart rate, either because the heart's natural pacemaker is not fast enough, or because there is a block in the heart's electrical conduction system. Arrhythmias are problems with the rate or rhythm of the heartbeat. During an arrhythmia, the heart can beat too fast, too slow, or with an irregular rhythm.

Most conventional pacemakers have two parts. One part is the generator containing a battery and the electrical circuitry to control the heartbeat. Another part are one or more leads. Leads are wires that connect the heart to the generator and carry the electrical signals to and from the heart. The leads detect the heart's rhythm contractions and send corresponding signals to the controller of the generator. Also, the leads carry the pacing pulses from the generator to the myocardium.

Modern pacemakers are externally programmable and allow a cardiologist to select the optimum pacing modes for individual patients. Some combine a pacemaker and defibrillator in a single implantable device. Others have multiple electrodes stimulating differing positions within the heart to improve the atrioventricular synchronization of the heart.

SUMMARY

This document provides devices and methods for artificial cardiac pacing and/or resynchronization. For example, this document provides improved electrodes for stimulating and sensing electrical activity of the heart, and to pacing and resynchronization systems incorporating such electrodes.

In one aspect, a cardiac pacing device includes a first flange portion; a second flange portion; a central portion extending between and connecting the first flange portion and the second flange portion; and one or more pacing electrodes exposed on an inward-facing surface of the first flange portion that faces the second flange portion.

Such a cardiac pacing device may optionally include one of more of the following features. The cardiac pacing device may also include one or more pacing electrodes exposed on an inward-facing surface of the second flange portion that faces the first flange portion. The cardiac pacing device may also include one or more resynchronization coils exposed on the inward-facing surface of the first flange portion that faces the second flange portion. The cardiac pacing device may also include one or more conductive leads extending from the cardiac pacing device (the one or more conductive leads in electrical communication with the one or more pacing electrodes), and a pulse generator attached to the one or more conductive leads and configured for sending electrical pulses for cardiac pacing via the one or more conductive leads to the one or more pacing electrodes. The cardiac pacing device may also include a wireless receiver configured for wireless communication with a controller separated from the cardiac pacing device. The controller may wirelessly communicate to the cardiac pacing device to control the cardiac pacing device. The cardiac pacing device may also include a controller circuitry coupled housed in the cardiac pacing device. The cardiac pacing device may be a fully self-contained pacing device. The cardiac pacing device may also include one or more pressure sensors coupled to the cardiac pacing device and configured for detecting a fluid pressure adjacent the cardiac pacing device. The one or more pressure sensors may include a first pressure sensor coupled to the first flange portion and a second pressure sensor coupled to the second flange portion. The first pressure sensor may be configured to detect a fluid pressure in a first heart chamber. The second pressure sensor may be configured to detect a fluid pressure in a second heart chamber that differs from the first heart chamber. The first heart chamber and the second heart chamber may be either both atria or both ventricles.

In another aspect, a method of treating a human heart by implanting a pacing device in the heart is provided. The pacing device includes a first flange portion; a second flange portion; a central portion extending between and connecting the first flange portion and the second flange portion; and one or more pacing electrodes exposed on an inward-facing surface of the first flange portion that faces the second flange portion. The first flange portion is disposed in a first heart chamber, the second flange portion is disposed in a second heart chamber that differs from the first heart chamber, and the central portion is disposed in a septal wall separating the first heart chamber from the second heart chamber.

Such a method of treating a human heart by implanting a pacing device in the heart may optionally include one or more of the following features. The one or more pacing electrodes of the first flange portion may be adjacent the septal wall. The pacing device may also include one or more pacing electrodes exposed on an inward-facing surface of the second flange portion that faces the first flange portion. The one or more pacing electrodes of the second flange portion may be adjacent the septal wall. The first heart chamber and the second heart chamber may be each atria. The first heart chamber and the second heart chamber may be each ventricles. The pacing device may be collapsible for deployment using a delivery sheath and may be self-expandable upon emergence from the delivery sheath.

In another aspect, a method of treating a human heart by implanting a pacing device in the heart is provided. The pacing device includes a first flange portion; a second flange portion; a central portion extending between and connecting the first flange portion and the second flange portion; and one or more pacing electrodes exposed on an inward-facing surface of the first flange portion that faces the second flange portion. The first flange portion is disposed in a first heart chamber, the second flange portion is disposed in a pericardial cavity, and the central portion is disposed in a myocardium separating the first heart chamber from the pericardial cavity.

Such a method of treating a human heart may optionally include one or more of the following features. The pacing device may also include one or more pacing electrodes exposed on an inward-facing surface of the second flange portion that faces the first flange portion. The one or more pacing electrodes of the first flange portion and of the second flange portion may be adjacent the myocardium.

In another aspect, a method of treating a human heart by implanting a pacing device in the heart is provided. The pacing device includes: a first flange portion; a second flange portion; a central portion extending between and connecting the first flange portion and the second flange portion; and one or more pacing electrodes exposed on an inward-facing surface of the first flange portion that faces the second flange portion. The first flange portion is disposed in an atrial appendage of the heart, the second flange portion is disposed in a ventricular outflow tract of the heart, and the central portion is disposed in a myocardium separating the appendage from the outflow tract.

Such a method of treating the human heart may optionally include one or more of the following features. The atrial appendage may be a right atrial appendage and the ventricular outflow tract may be a right ventricular outflow tract. The atrial appendage may be a left atrial appendage and the ventricular outflow tract may be a left ventricular outflow tract.

Particular embodiments of the subject matter described in this document can be implemented to realize one or more of the following advantages. First, the designs provided herein facilitate stable, reliable anchoring of electrodes in relation to the myocardium. Second, in some cases the devices provided herein function as a dual-purpose device, i.e., as an occluder and as an electrode/coil carrying device for pacing and/or resynchronization. Third, in some cases the devices provided herein facilitate atrioventricular pacing using a single device implanted in a single location. Fourth, while placing conventional leads in a thin septum/membrane has been known to cause defects, the systems and methods provided herein create an opening in a controlled manner and then seals the opening. Fifth, the devices and methods provided herein facilitate pacing in specific desirable conduction system areas. Sixth, in some cases the devices and methods provided herein allow for painless cardiac defibrillation. Seventh, in some embodiments mechanical device linkages are created that can be advantageous for clot prevention during fibrillation. In some embodiments, various heart conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Pulse generation which causes contraction of the selected chamber is termed "capture." Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices and methods for artificial cardiac pacing and/or resynchronization. For example, this document provides improved electrodes for stimulating and sensing electrical activity of the heart, and provides pacing and resynchronization systems incorporating such electrodes. While the devices and methods provided herein are described primarily in the context of pacing, it should be understood that resynchronization can additionally or alternatively be performed in an analogous manner, and that the scope of this disclosure includes such subject matter.

In some embodiments, the devices provided herein are well-suited to providing specific conduction system pacing, i.e., in specific desirable cardiac conduction system areas. For example, as described further below, some embodiments provided herein provide pacing in specific desirable conduction system areas such as, but not limited to the His bundle, the penetrating bundle of His, the proximal conduction system, to provide a few examples. For example, in some embodiments the distal end of the cardiac pacing and/or resynchronization electrode-carrying cardiac device can be located in the right ventricular outflow tract and the device can curve around the crista supraventricularis such that the proximal end of the device is located in the atrium. In some cases, such an implementation would facilitate specific conduction system capture and sensing in addition to atrial and ventricular pacing.

One skilled in the art will perceive that the devices described herein can provide multiple treatment modalities using a single device. For example, some embodiments of the devices provided herein are dual-purpose devices, i.e., functioning as an occluder device and as an electrode/coil carrying device for pacing and/or resynchronization. In one example implementation, some devices described herein can be implanted in a patent foramen ovale (PFO). In addition to closing/occluding the PFO, the device can provide pacing and/or resynchronization.

In some embodiments, the devices provided herein are configured to be retrievable. For example, in some embodiments the devices provided herein can be recaptured into the lumen of a catheter/sheath and removed from the patient endovascularly. In some embodiments, the devices provided herein can be retrieved using a subcutaneous retrieval technique.

Figure 1:
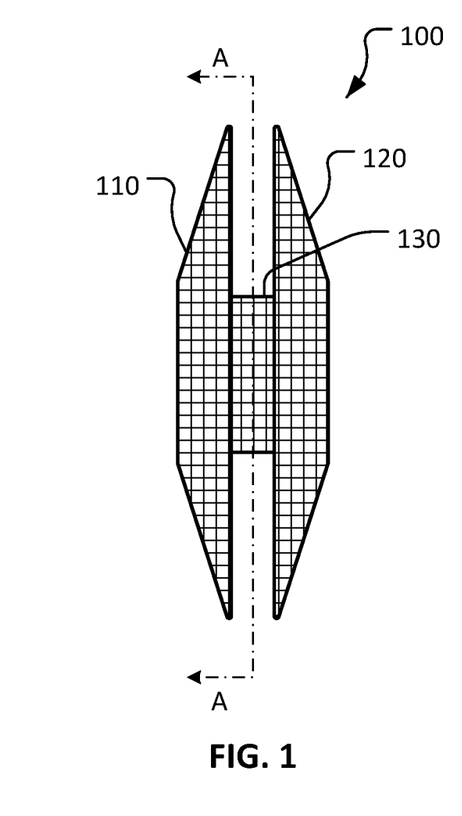
FIG. 1 is a side view of an example cardiac pacing and/or resynchronization electrode-carrying device in accordance with some embodiments provided herein.
Figure 2:
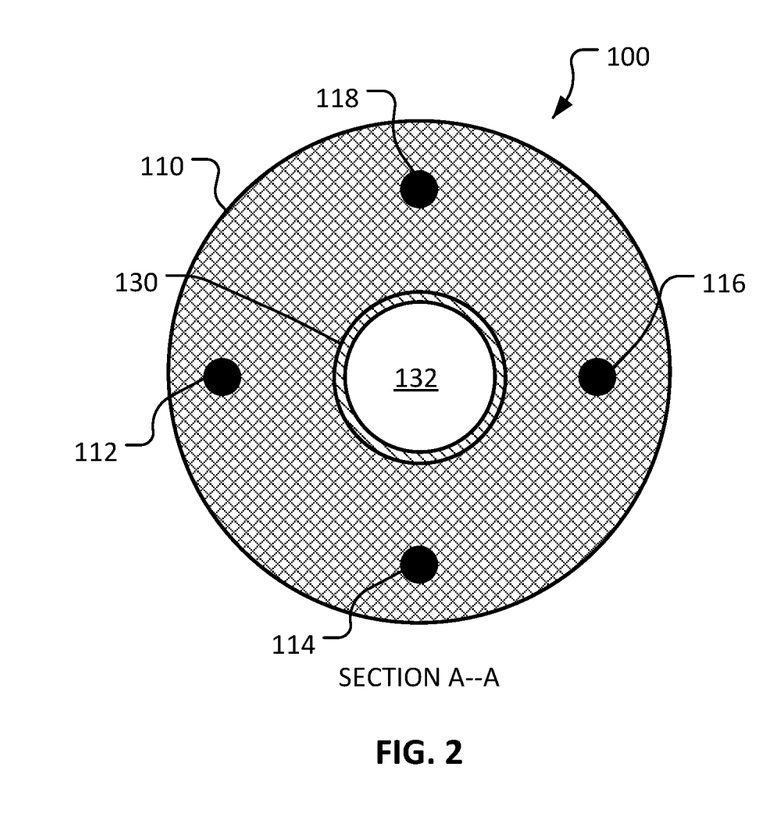
FIG. 2 is a cross-sectional view of the cardiac pacing and/or resynchronization electrode-carrying device of FIG. 1.

Referring to FIGS. 1 and 2, an example cardiac pacing and/or resynchronization electrode-carrying cardiac device 100 (hereinafter referred to as "pacing device 100") can be adapted for advantageous human use in multiple different manners, as described herein. Pacing device 100 includes a first flange portion 110, a second flange portion 120, and a central connecting portion 130. In some cases, portions 110, 120, and 130 are integrally constructed. In some cases, portions 110, 120, and 130 are initially constructed separately and then joined together.

Pacing device 100 is configured for deployment in a minimally-invasive manner. That is, pacing device 100 is diametrically collapsible so that pacing device 100 can be deployed in vivo from a lumen of a low-profile catheter/sheath. Pacing device 100 is shown in its expanded configuration. That is, in some embodiments pacing device 100 will self-expand to the approximate shape shown when relieved from the diametric constraints of a catheter/sheath. Pacing device 100 may become elongated when diametrically collapsed to its low-profile configuration.

In some embodiments, pacing device 100 is made of a framework of one or more elongate members (e.g., wires, struts, and the like). For example, in some embodiments pacing device 100 is made of one or more metallic wires that are braided or woven and then shape-set into the configuration shown. In another example, in some embodiments pacing device 100 is made of a cut-tube of material that is then expanded and shape-set into the configuration shown. In some embodiments, a metal such as Nitinol or stainless steel is used for the framework of pacing device 100. In some embodiments, one or more radiopaque (RO) markers may be included on various locations of the pacing device 100.

Pacing device 100 is compliant, elastic, and flexible so as to conform to the sometimes irregular topography of the tissue that it may be in contact with. Moreover, pacing device 100 is designed to maintain robust tissue contact in spite of the dynamic tissue topography associated with the cardiac cycle.

In some embodiments, pacing device 100 include features directed to enhancing migration resistance such as, but not limited to, macro anchor features (e.g., prongs, hooks, barbs, atraumatic probes, spikes, etc.) or micro anchor features (e.g., a grouping of small protrusions, surface texturing, etc.). One or more mechanical features such as hooks, rings, lassos, tethers, eyelets, and the like can be included on pacing device 100 to facilitate deployment, repositioning, and/or retrieval of pacing device 100.

In some embodiments, a covering material may be included on portions of pacing device 100. Such a covering material may be made of materials including, but not limited to, PTFE, ePTFE, DACRON, and the like. In some cases, the covering material may enhance the occlusive properties of pacing device 100. In some cases, the covering material may be treated to enhance tissue growth, and promote encapsulation and endothelialization of tissue to encourage anatomical closure of a tissue aperture. In some embodiments, the covering can be modified by one or more chemical or physical processes that enhance certain physical properties of the covering. For example, a hydrophilic coating may be applied to the covering to improve the wettability and echo translucency of the covering. In some embodiments, the covering may be modified with chemical moieties that promote one or more of endothelial cell attachment, endothelial cell migration, endothelial cell proliferation, and resistance to thrombosis. In some embodiments, the covering may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

Pacing device 100 can include one or more pacing electrodes and/or resynchronization coils. In the depicted example embodiment, first flange portion 110 includes four electrodes 112, 114, 116, and 118. As described further below, electrodes 112, 114, 116, and 118 are disposed on the tissue-contacting surface of first flange portion 110 that is inward-facing and that faces second flange portion 120. In some embodiments, electrodes are included only on one portion (either on first flange portion 110 or second flange portion 120) of pacing device 100. In some embodiments, electrodes are included on both portions (on first flange portion 110 and on second flange portion 120) of pacing device 100. Any number of electrodes can be included.

It should be understood that any configuration of a wide variety of possible electrode/coil configurations can be used for pacing device 100, and all such configurations are within the scope of this disclosure. For example, in some embodiments pacing device 100 is configured as a unipolar pacing device. That is, in some embodiments the one or more electrodes of pacing device 100 are cathode(s) electrode(s), and a remotely implanted pulse generator module acts as an anode electrode. In some embodiments, pacing device 100 is configured as a bipolar device. That is, in some embodiments one or more electrodes on one portion of the device (either on first flange portion 110 or second flange portion 120) are cathode(s) and one or more electrodes on the opposite portion of the device are anode(s).

The pulse generation and other control aspects for operating pacing device 100 can originate from various devices and by various technical manners. Any and all such different iterations are within the scope of this disclosure. For example, in some embodiments pacing device 100 is connected via one or more leads to a remotely implanted pulse generator/controller. In some embodiments, pacing device 100 is a wireless pacing device. As a wireless pacing device, pacing device 100 can utilize active RF technology, passive RF technology, or technology by which both pacing device 100 and a remote generator/controller can transmit and receive communications.

In some embodiments, pacing device 100 is fully self-contained. That is, in some embodiments the componentry of a generator/controller can be integrally contained in pacing device 100. For example, in some embodiments pacing device 100 includes an interior space 132 defined by central connecting portion 130 that can house such componentry of a generator/controller.

In some embodiments, pacing device 100 is configured only for cardiac pacing. In some embodiments, pacing device 100 is configured for performance of resynchronization only. In some embodiments, pacing device 100 is configured for both cardiac pacing and resynchronization.

Figure 3:
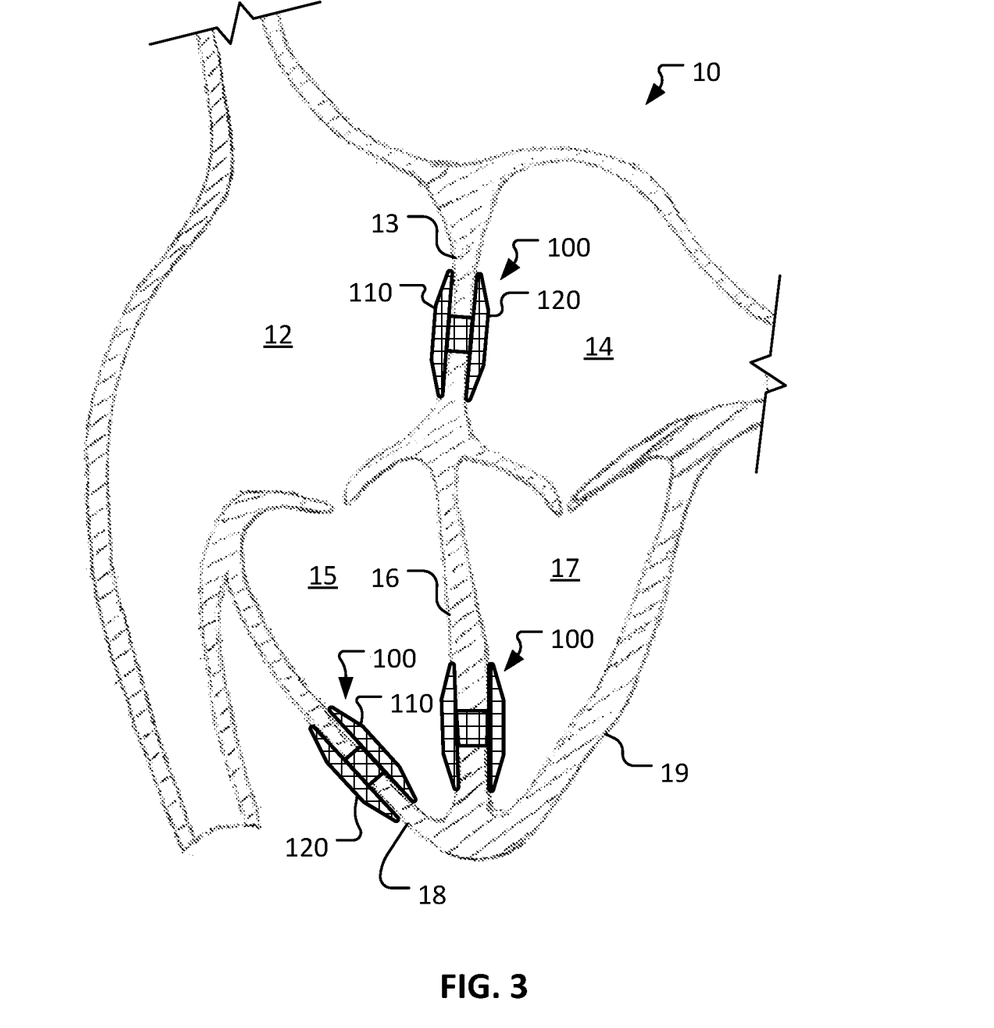
FIG. 3 is a schematic cross-sectional view of a human heart with example cardiac pacing and/or resynchronization electrode-carrying devices implanted in various areas of the heart.

Referring also to FIG. 3, pacing device 100 can be implanted in a human heart 10 in a number of different locations, and using a number of different deployment techniques. Only some of the possible advantageous deployment locations are illustrated here. Heart 10 includes a right atrium 12, an atrial septum 13, a left atrium 14, a right ventricle 15, a ventricular septum 16, a left ventricle 17, a right ventricular free wall 18, and a left ventricular free wall 19.

In a first example, pacing device 100 can be implanted in atrial septum 13. Accordingly, first flange portion 110 is disposed in right atrium 12 and second flange portion 120 is disposed in left atrium 14. The one or more electrodes 112, 114, 116, and 118 are in contact with atrial septum 13. Such an arrangement can provide, in some cases, compact AV nodal stimulation, and/or synchronous atrial stimulation, to provide a couple of examples.

In some cases, central connecting portion 130 of pacing device 100 is implanted in an aperture that is created for the purpose of implanting pacing device 100. Alternatively, in some cases pacing device 100 is advantageously implanted in a previously existing aperture such as a PFO or other type of septal/membrane defect. In such a case, pacing device 100 performs the dual-purpose of pacing/resynchronization and occlusion.

In another example, pacing device 100 can be implanted in ventricular septum 16. Accordingly, first flange portion 110 is disposed in right ventricle 15 and second flange portion 120 is disposed in left ventricle 17. The one or more electrodes 112, 114, 116, and 118 are in contact with ventricular septum 16. Such an arrangement can provide, ventricular stimulation and or resynchronization.

In some cases, in order to obviate or minimize the need for making a septal puncture, pacing device 100 can be implanted in a Thebesian vein of ventricular septum 16. Such a deployment can be performed, for example, using a Doppler sensor on a wire to detect the location of a Thebesian vein in ventricular septum 16. Thereafter, the wire can be used to penetrate the Thebesian vein and one or more other deployment devices can be used over the wire to deploy pacing device 100.

In another example, pacing device 100 can be implanted in right ventricular free wall 18 (or in left ventricular free wall 19). Accordingly, first flange portion 110 is disposed in right ventricle 15 and second flange portion 120 is disposed in the pericardial cavity. The one or more electrodes 112, 114, 116, and 118 are in contact with ventricular free wall 18 (on either surface of ventricular free wall 18, i.e., the epicardial surface or the endocardial surface).

In still another example, pacing device 100 can be implanted between an atrial appendage and a ventricular outflow tract. For example, the implanted arrangement can be either between the right atrial appendage and the right ventricular outflow tract, or between the left atrial appendage and the left ventricular outflow tract. Accordingly, first flange portion 110 is disposed in right or left atrial appendage and second flange portion 120 is disposed in the right or left ventricular outflow tract, respectively. While these arrangements are not illustrated, one of skill in the art will understand the arrangements based on the description. In these arrangements, pacing device 100 will function as an atrioventricular pacing and/or resynchronization device. That is, pacing device 100 will provide pacing and/or resynchronization for both atrial and ventricular chambers of heart 10.

In yet another example, pacing device 100 can be implanted through the right atrial appendage and into the right ventricular outflow tract. This implementation will provide the capability of atrioventricular pacing without crossing the tricuspid valve. Moreover, the outflow tract tends to produce more synchronous biventricular pacing than other sites. The deployment procedure would involve the trans-catheter device that facilitates the entry of a transseptal-like needle via the right atrial appendage into the right outflow tract. Then, a small wire would be passed from the right outflow tract into the right atrial appendage. For guidance, an expandable or flat deflectable component with or without magnet aid in the right atrial appendage can be used. Such a device would serve to maximize apposition to the right ventricular outflow tract while passing the wire and deploying the device. This technique for deploying pacing device 100 into the right ventricular outflow tract would decrease the potential for bleeding into the pericardial space.

Pacing device 100 can be implanted using various minimally invasive or surgical techniques. For example, in some cases pacing device 100 can be placed using an endocardial approach via vascular access. In such a case, femoral veins, subclavian veins, internal jugular veins, and the like, can be used for transvenous access. In some cases, an epicardial approach can be used to place pacing device 100. In such a case, subxiphoid or intercostal accesses can be used for example. In some cases, pacing device 100 can be implanted using an open chest surgical technique. Moreover, in some cases a guidewire, along with a puncture needle, is inserted into the vasculature, internally snared, and then pulled out of the patient so that both ends of the guidewire are controlled using a counter-traction technique. In such a case, pacing device 100 can be then implanted using either an inside out technique, or an outside in technique.

In some embodiments, pacing device 100 can also be equipped with various other features that can extend the functionality provided be pacing device 100. For example, in some embodiments pacing device 100 can include one or more pressure sensors for detecting pressures on first flange portion 110 and/or second flange portion 120. In some such cases, the measured pressure(s) can be used as inputs of an algorithm of the control circuitry of pacing device 100 to modify the pacing scheme (e.g., adjust which electrode(s) 112, 114, 116, and/or 118 are being used for stimulation, adjust pulse timing, and the like).

In some embodiments, pacing device 100 can also be equipped with piezoelectric crystals and/or tissue Doppler devices to sense myocardial performance. Signals from such devices can be used for aspects such as, but not limited to, early myocardial infarction (MI) detection, and/or to change the pacing vector to improve myocardial performance.

In some embodiments, pacing device 100 can also be equipped with one or more electromagnets. In addition, in some embodiments electromagnets can be positioned in one or more other locations in heart 10 that are spaced apart from pacing device 100. Then, the electromagnets can be activated and/or deactivated to induce myocardial movement. Such movement can help prevent thrombus formation, for example, during fibrillation.

Figure 4:
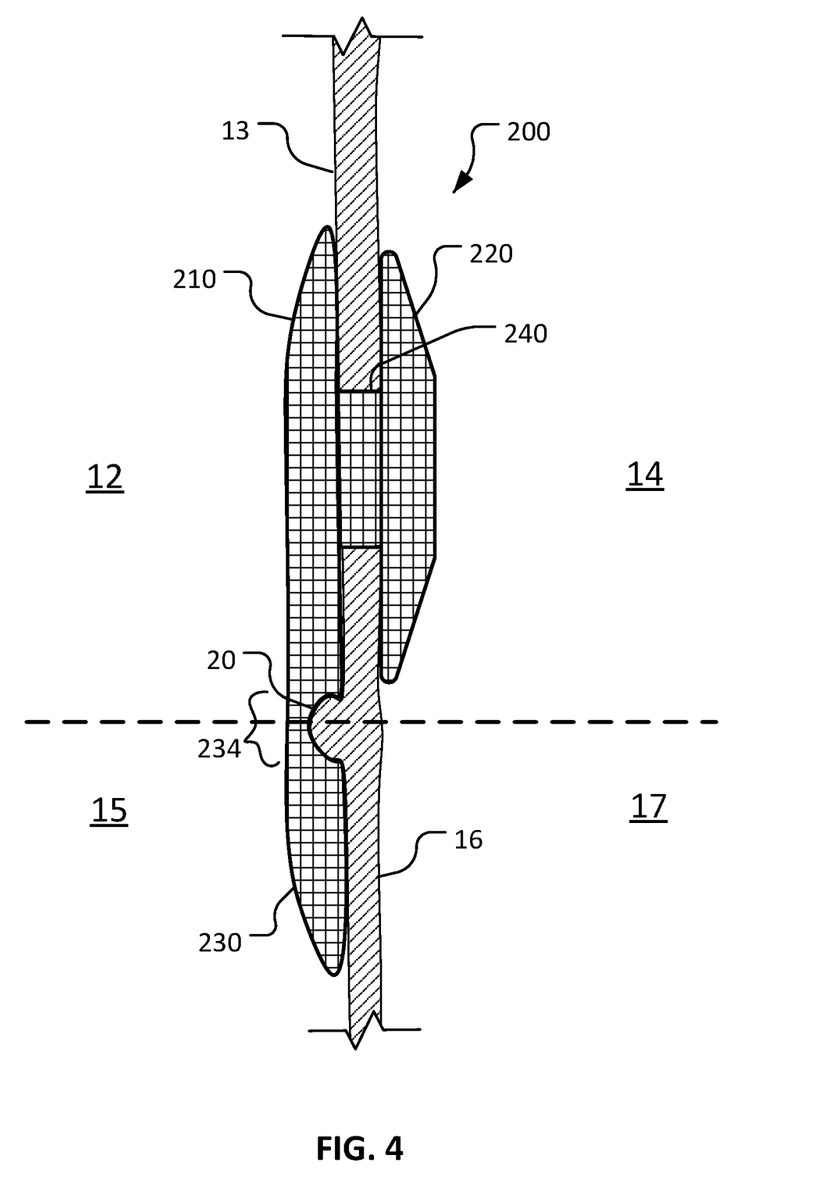
FIG. 4 is a schematic cross-sectional view of a human heart with another example cardiac pacing and/or resynchronization electrode-carrying device implanted in the heart.

Referring to FIG. 4, another example cardiac pacing and/or resynchronization electrode-carrying cardiac device 200 (hereinafter referred to as "pacing device 200") can be adapted for advantageous human use in multiple different manners, as described herein. Pacing device 200 includes a first flange portion 210, a second flange portion 220, a third flange portion 230, a transvalvular connecting portion 234, and a transseptal connecting portion 240. Transvalvular connecting portion 234 extends between first flange portion 210 and third flange portion 230. Transseptal connecting portion 240 extends between first flange portion 210 and second flange portion 220.

Pacing device 200 is a tri-flanged device. In some cases (as depicted), first flange portion 210 is disposed in right atrium 12 and is in contact with the atrial septum 13. Second flange portion 220 is disposed in left atrium 14 and is in contact with the atrial septum 13. Third portion 230 is disposed in right ventricle 15 and is in contact with ventricular septum 16. Other arrangements are also envisioned. For example, first flange portion 210 can be disposed in left atrium 14, second flange portion 220 can be disposed in right atrium 12, and third portion 230 can be disposed in left ventricle 17.

In the depicted arrangement, transvalvular connecting portion 234 extends through the tricuspid valve, generally adjacent to an anterior tricuspid valve annulus 20. In some cases, transvalvular connecting portion 234 is configured to extend through a commissure of the valve's leaflets. Pacing device 200 is configured to not contribute to valvular regurgitation.

The use of pacing device 200 facilitates specific His bundle pacing either on the membranous septum 16 or in the distal AV node transitional zone with or without being able to sense and pace atrial and ventricular myocardium at the same time.

In some cases, portions 210, 220, 230, and 240 are integrally constructed. In some cases, one or more of the portions 210, 220, 230, and 240 are initially constructed separately and then joined together.

Pacing device 200 is configured for deployment in a minimally-invasive manner. That is, pacing device 200 is diametrically collapsible so that pacing device 200 can be deployed in vivo from a lumen of a low-profile catheter/sheath. Pacing device 200 is shown in its expanded configuration. That is, in some embodiments pacing device 200 will self-expand to the approximate shape shown when relieved from the diametric constraints of a catheter/sheath. Pacing device 200 may become elongated when diametrically collapsed to its low-profile configuration.

In some embodiments, pacing device 200 is made of a framework of one or more elongate members (e.g., wires, struts, and the like). For example, in some embodiments pacing device 200 is made of one or more metallic wires that are braided or woven and then shape-set into the configuration shown. In another example, in some embodiments pacing device 200 is made of a cut-tube of material that is then expanded and shape-set into the configuration shown. In some embodiments, a metal such as Nitinol or stainless steel is used for the framework of pacing device 200. In some embodiments, one or more RO markers may be included on various locations of the pacing device 200.

Pacing device 200 is compliant, elastic, and flexible so as to conform to the sometimes irregular topography of the tissue that it may be in contact with. Moreover, pacing device 200 is designed to maintain robust tissue contact in spite of the dynamic tissue topography associated with the cardiac cycle.

In some embodiments, pacing device 200 include features directed to enhancing migration resistance such as, but not limited to, macro anchor features (e.g., prongs, hooks, barbs, atraumatic probes, spikes, etc.) or micro anchor features (e.g., a grouping of small protrusions, surface texturing, etc.). One or more mechanical features such as hooks, rings, lassos, tethers, eyelets, and the like can be included on pacing device 200 to facilitate deployment, repositioning, and/or retrieval of pacing device 200.

In some embodiments, pacing device 200 is configured only for cardiac pacing. In some embodiments, pacing device 200 is configured for performance of resynchronization only. In some embodiments, pacing device 200 is configured for both cardiac pacing and resynchronization.

The flange portions 210, 220, and 230 of pacing device 200 can include one or more pacing electrodes and/or resynchronization coils like described above in reference to pacing device 100. In some embodiments, electrodes are included only on one or two flange portions 210, 220, and/or 230 of pacing device 200. In some embodiments, electrodes are included on all portions 210, 220, and 230 of pacing device 200. Any number of electrodes can be included.

It should be understood that any configuration of a wide variety of possible electrode/coil configurations can be used for pacing device 200, and all such configurations are within the scope of this disclosure. For example, in some embodiments pacing device 200 is configured as a unipolar pacing device. That is, in some embodiments the one or more electrodes of pacing device 200 are cathode(s) electrode(s), and a remotely implanted pulse generator module acts as an anode electrode. In some embodiments, pacing device 200 is configured as a bipolar device. That is, in some embodiments one or more electrodes on one portion of the device (either on first flange portion 210, second flange portion 220, and/or third flange portion 230) are cathode(s) and one or more electrodes on the opposite portion of the device are anode(s).

The pulse generation and other control aspects for operating pacing device 200 can originate from various devices and by various technical manners. Any and all such different iterations are within the scope of this disclosure. For example, in some embodiments pacing device 200 is connected via one or more leads to a remotely implanted pulse generator/controller. In some embodiments, pacing device 200 is a wireless pacing device. As a wireless pacing device, pacing device 200 can utilize active RF technology, passive RF technology, or technology by which both pacing device 200 and a remote generator/controller can transmit and receive communications.

In some embodiments, pacing device 200 is fully self-contained. That is, in some embodiments the componentry of a generator/controller can be integrally contained in pacing device 200. For example, in some embodiments pacing device 200 includes an interior space defined by transseptal connecting portion 240 that can house such componentry of a generator/controller.

In some embodiments, pacing device 200 is configured only for cardiac pacing. In some embodiments, pacing device 200 is configured for performance of resynchronization only. In some embodiments, pacing device 200 is configured for both cardiac pacing and resynchronization.

Figure 5:
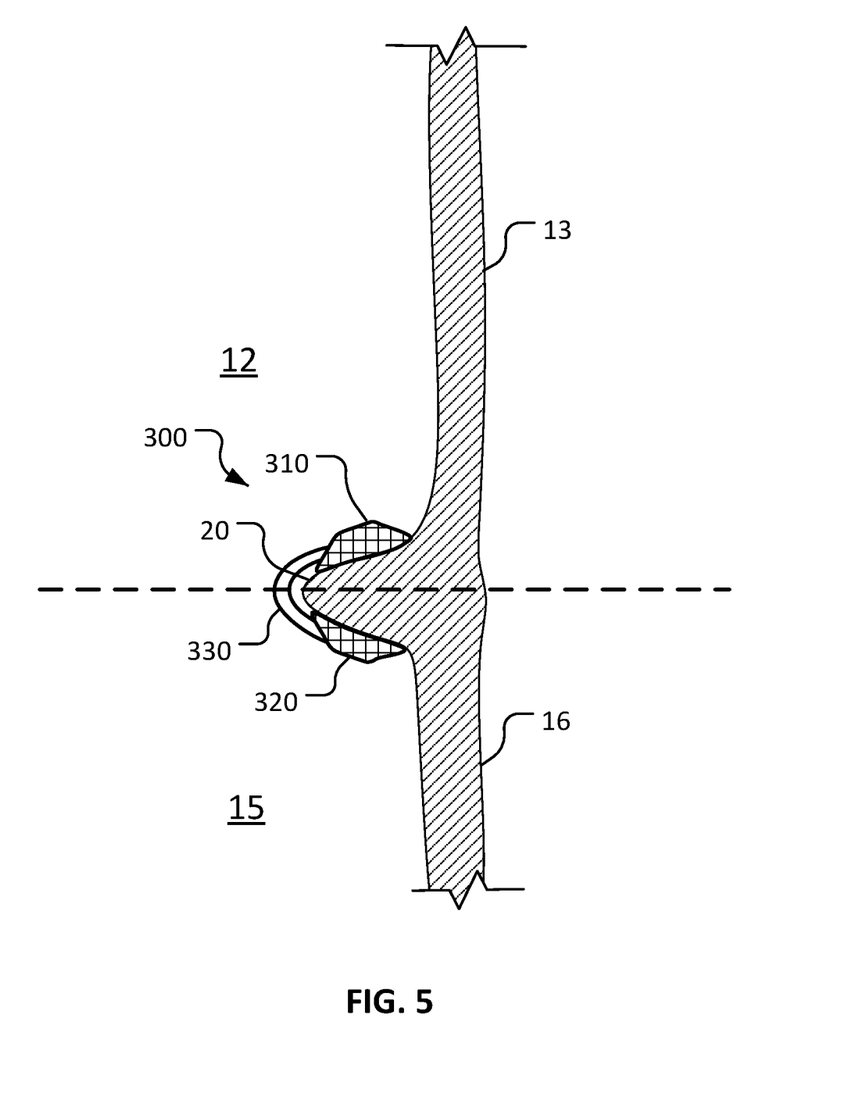
FIG. 5 is a schematic cross-sectional view of a human heart with another example cardiac pacing and/or resynchronization electrode-carrying device implanted in the heart.

Referring to FIG. 5, another example cardiac pacing and/or resynchronization electrode-carrying cardiac device 300 (hereinafter referred to as "pacing device 300") can be adapted for advantageous human use in multiple different manners, as described herein. Pacing device 300 includes a first flange portion 310, a second flange portion 320, and a transvalvular connecting portion 330. Transvalvular connecting portion 330 extends between first flange portion 310 and second flange portion 320.

In the depicted arrangement, transvalvular connecting portion 330 extends through the tricuspid valve, generally adjacent to an anterior tricuspid valve annulus 20. Pacing device can also be used for the mitral valve. In some cases, transvalvular connecting portion 330 is configured to extend through a commissure of the valve's leaflets. Pacing device 300 can be placed anywhere on a valve annulus, and can also be placed in other locations such as, but not limited to, epicardially on the left atrial appendage or the right atrial appendage. Pacing device 300 is configured to not substantially contribute to valvular regurgitation.

In some embodiments, first flange portion 310 includes electrodes (or coils) that are on the atrial myocardium near the high septal annulus. In some embodiments, second flange portion 320 includes one or more electrodes (or coils) on the ventricular side of the annulus in a similar location. Pacing device 300 leverages the fact that the annulus and the fibrous skeleton of the heart are smaller in circumference and diameter than the neighboring atrial and ventricular myocardium allowing pacing device 300 to be deployable. This type of leadless device deployment and stability can be used in other regions as well.

Pacing device 300 is configured for deployment in a minimally-invasive manner. That is, pacing device 300 is diametrically collapsible so that pacing device 300 can be deployed in vivo from a lumen of a low-profile catheter/sheath. Pacing device 300 is shown in its expanded configuration. That is, in some embodiments pacing device 300 will self-expand to the approximate shape shown when relieved from the diametric constraints of a catheter/sheath. Pacing device 300 may become elongated when diametrically collapsed to its low-profile configuration.

In some embodiments, pacing device 300 is made of a framework of one or more elongate members (e.g., wires, struts, and the like). For example, in some embodiments pacing device 300 is made of one or more metallic wires that are braided or woven and then shape-set into the configuration shown. In another example, in some embodiments pacing device 300 is made of a cut-tube of material that is then expanded and shape-set into the configuration shown. In some embodiments, a metal such as Nitinol or stainless steel is used for the framework of pacing device 300. In some embodiments, one or more RO markers may be included on various locations of the pacing device 300.

Pacing device 300 is compliant, elastic, and flexible so as to conform to the sometimes irregular topography of the tissue that it may be in contact with. Moreover, pacing device 300 is designed to maintain robust tissue contact in spite of the dynamic tissue topography associated with the cardiac cycle.

In some embodiments, pacing device 300 include features directed to enhancing migration resistance such as, but not limited to, macro anchor features (e.g., prongs, hooks, barbs, atraumatic probes, spikes, etc.) or micro anchor features (e.g., a grouping of small protrusions, surface texturing, etc.). One or more mechanical features such as hooks, rings, lassos, tethers, eyelets, and the like can be included on pacing device 300 to facilitate deployment, repositioning, and/or retrieval of pacing device 300.

In some embodiments, pacing device 300 is configured only for cardiac pacing. In some embodiments, pacing device 300 is configured for performance of resynchronization only. In some embodiments, pacing device 300 is configured for both cardiac pacing and resynchronization.

The flange portions 310 and 320 of pacing device 300 can include one or more pacing electrodes and/or resynchronization coils like described above in reference to pacing device 100. In some embodiments, electrodes are included only on one flange portion 310 or 320 of pacing device 300. In some embodiments, electrodes are included both portions 310 and 320 of pacing device 300. Any number of electrodes can be included.

It should be understood that any configuration of a wide variety of possible electrode/coil configurations can be used for pacing device 300, and all such configurations are within the scope of this disclosure. For example, in some embodiments pacing device 300 is configured as a unipolar pacing device. That is, in some embodiments the one or more electrodes of pacing device 300 are cathode(s) electrode(s), and a remotely implanted pulse generator module acts as an anode electrode. In some embodiments, pacing device 300 is configured as a bipolar device. That is, in some embodiments one or more electrodes on one portion of the device (either on first flange portion 310 and/or second flange portion 320) are cathode(s) and one or more electrodes on the opposite portion of the device are anode(s).

The pulse generation and other control aspects for operating pacing device 300 can originate from various devices and by various technical manners. Any and all such different iterations are within the scope of this disclosure. For example, in some embodiments pacing device 300 is connected via one or more leads to a remotely implanted pulse generator/controller. In some embodiments, pacing device 300 is a wireless pacing device. As a wireless pacing device, pacing device 300 can utilize active RF technology, passive RF technology, or technology by which both pacing device 300 and a remote generator/controller can transmit and receive communications.

In some embodiments, pacing device 300 is fully self-contained. That is, in some embodiments the componentry of a generator/controller can be integrally contained in pacing device 300. For example, in some embodiments pacing device 300 includes an interior space defined by transvalvular connecting portion 330 that can house such componentry of a generator/controller.

In some embodiments, pacing device 300 is configured only for cardiac pacing. In some embodiments, pacing device 300 is configured for performance of resynchronization only. In some embodiments, pacing device 300 is configured for both cardiac pacing and resynchronization.

It is also envisioned that a pacing device with the two-part characteristics of pacing device 300 can be used to approximate cardiac structures for pacing and/or resynchronization purposes. For example, in one such exemplary implementation a first portion of the clamshell-like structure can be secured to/against the left atrial appendage and the second portion can be either kept free or secured to/against the right atrial appendage. In this implementation, no cardiac structures are punctured, while the implementation helps facilitate multisite pacing of structure(s) not easy to otherwise pace.

It should be understood that one or more features from a particular embodiment described herein can be combined with one or more features from one or more other embodiments described herein. Hence, all such possible hybrid designs are envisioned within the scope of this disclosure.

Another design iteration that can be incorporated in any of the pacing device embodiments described herein is to make the devices of two materials (e.g., could be two types of nitinol). The first type of material (which, for example, could be near a septal puncture site and/or distally on the circumflex) would be a softer material that is less traumatic, and would not have the electrode components which would necessarily add stiffness. Such a soft material would serve as something as a buttress and hemostatic mechanism while the stiffer portion that includes electrode components will allow for sensing in the pacing and/or defibrillation while maintaining stability and contact. Another design variation can include deployable buttresses or "skirts" that can be activated by an external magnet or an internal deployment device that would be separate from what is left behind, in case bleeding or lack of stability is noted after implant.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of treating a human heart, wherein the method comprises implanting a pacing device in the heart, wherein the pacing device comprises:
    a first flange portion;
    a second flange portion;
    a central portion extending between and connecting the first flange portion and the second flange portion, the central portion comprising a framework of one or more elongate members that are braided or woven;
    controller and generator componentry housed in the pacing device such that the pacing device is a fully self-contained and leadless pacing device; and
    one or more pacing electrodes exposed on an inward-facing surface of the first flange portion that faces the second flange portion,
    wherein the first flange portion is disposed in a first heart chamber, the second flange portion is disposed in a second heart chamber that differs from the first heart chamber, and the central portion is disposed in a septal wall separating the first heart chamber from the second heart chamber.

2. The method of claim 1, wherein the one or more pacing electrodes of the first flange portion are adjacent the septal wall.

3. The method of claim 2, wherein the pacing device further comprises one or more pacing electrodes exposed on an inward-facing surface of the second flange portion that faces the first flange portion, and wherein the one or more pacing electrodes of the second flange portion are adjacent the septal wall.

4. The method of claim 1, wherein the first heart chamber and the second heart chamber are each atria.

5. The method of claim 1, wherein the first heart chamber and the second heart chamber are each ventricles.

6. The method of claim 1, wherein the pacing device is collapsible for deployment using a delivery sheath and is self-expandable upon emergence from the delivery sheath.

7. The method of claim 1, wherein the central portion is disposed in a patent foramen ovale.

8. The method of claim 1, wherein the implanting comprises joining together at least one of the first flange portion, second flange portion, or central portion with other portions of the pacing device.

9. The method of claim 1, further comprising pacing the heart using the one or more pacing electrodes.

10. The method of claim 1, further comprising resynchronizing the heart using the one or more pacing electrodes.

11. The method of claim 1, wherein the pacing device further comprises a pressure sensor attached to the first flange portion or the second flange portion, and wherein the method further comprises detecting a pressure.

12. The method of claim 11, further comprising modifying a pacing scheme delivered by the one or more pacing electrodes based on the pressure detected by the pressure sensor.

13. The method of claim 1, wherein the pacing device further comprises piezoelectric crystals or Doppler devices to sense myocardial performance of the heart.

14. The method of claim 13, further comprising detecting early myocardial infarction (MI) detection based on signal outputs from the piezoelectric crystals or Doppler devices.

15. The method of claim 13, further comprising changing a pacing vector to improve myocardial performance based signal outputs from the piezoelectric crystals or Doppler devices.

16. The method of claim 1, wherein the controller and generator componentry is housed in the central portion of the pacing device.

17. The method of claim 1, wherein the pacing device further comprises one or more resynchronization coils exposed on the inward-facing surface of the first flange portion.

18. The method of claim 17, further comprising delivering both cardiac pacing and resynchronization to the human heart from the pacing device.

* * * * *